United States Patent
Borja

(10) Patent No.: US 7,312,256 B2
(45) Date of Patent: Dec. 25, 2007

(54) DENTURE LINER, DENTURE LINER KIT AND METHOD FOR MAKING A DENTURE LINER

(75) Inventor: Michael J. Borja, Keyport, NJ (US)

(73) Assignee: Combe Incorporated, White Plains, NY (US)

( * ) Notice: Subject to any disclaimer, the term of this patent is extended or adjusted under 35 U.S.C. 154(b) by 271 days.

(21) Appl. No.: 10/987,833

(22) Filed: Nov. 12, 2004

(65) Prior Publication Data

US 2006/0106128 A1 May 18, 2006

(51) Int. Cl.
*A61K 6/10* (2006.01)
*A61K 6/08* (2006.01)
*A61C 13/00* (2006.01)

(52) U.S. Cl. .................. 523/120; 433/168.1; 523/118
(58) Field of Classification Search ............... 523/120; 433/168.1
See application file for complete search history.

(56) References Cited

U.S. PATENT DOCUMENTS

| | | | |
|---|---|---|---|
| 2,854,746 A | 10/1958 | Lester et al. | |
| 2,978,812 A | 4/1961 | Rosenthal et al. | |
| 3,618,213 A | 11/1971 | Shepherd et al. | |
| 3,716,918 A | 2/1973 | Iole et al. | |
| 3,808,686 A | 5/1974 | Tauman et al. | |
| 3,833,518 A * | 9/1974 | Rubin et al. ................. | 523/118 |
| 3,969,303 A | 7/1976 | Prosen | |
| 4,270,904 A | 6/1981 | Bogaert | |
| 4,373,036 A | 2/1983 | Chang et al. | |
| 4,503,116 A | 3/1985 | Lapidus | |
| 4,514,173 A | 4/1985 | Re | |
| 4,619,891 A | 10/1986 | Takahashi | |
| 4,632,880 A | 12/1986 | Lapidus | |
| 4,670,480 A | 6/1987 | Morrone | |
| 4,705,836 A | 11/1987 | Ohtsuka et al. | |
| 4,764,115 A | 8/1988 | Willits et al. | |
| 5,001,170 A | 3/1991 | Keegan | |
| 5,030,094 A | 7/1991 | Nardi et al. | |
| 5,037,473 A | 8/1991 | Antonucci et al. | |
| 5,061,182 A | 10/1991 | Kubo et al. | |
| 5,073,604 A | 12/1991 | Holeva et al. | |
| 5,075,107 A | 12/1991 | Katakura et al. | |
| 5,155,252 A | 10/1992 | Yamamoto et al. | |
| 5,203,700 A | 4/1993 | Chmel | |
| 5,268,396 A | 12/1993 | Lai | |
| 5,282,746 A | 2/1994 | Sellers et al. | |
| 5,306,338 A | 4/1994 | Tsunekawa | |
| 5,338,190 A | 8/1994 | Tregillis | |
| 5,431,563 A | 7/1995 | Huybrechts, Robert | |
| 5,436,283 A | 7/1995 | Okada et al. | |
| 5,513,988 A | 5/1996 | Jeffer et al. | |
| 5,624,745 A | 4/1997 | Lapidus | |
| 5,678,993 A | 10/1997 | Jeffer et al. | |
| 5,880,172 A | 3/1999 | Rajaiah et al. | |
| 5,885,077 A | 3/1999 | Jeffer | |
| 6,350,794 B1 | 2/2002 | Borja | |
| 6,638,881 B2 | 10/2003 | Lapidus | |
| 2004/0028930 A1 | 2/2004 | Wong et al. | |

FOREIGN PATENT DOCUMENTS

EP 0 353 375 8/1988

OTHER PUBLICATIONS

International Search Report and The Written Opinion of the International Searching Authority, Aug. 5, 2006, 10 pages.
Graham et al., J. Prosthetic Dentistry, vol. 2, No. 4, pp. 422-428, Feb. 1989.

* cited by examiner

*Primary Examiner*—Tae H Yoon
(74) *Attorney, Agent, or Firm*—St. Onge Steward Johnston & Reens LLC

(57) ABSTRACT

A denture liner which includes a hydrophobic polymer component, a plasticizer component and an adhesive component. A method for making this denture liner and a denture liner kit are also provided. The compositions have improved consistency and are useful in prosthodontics, including formulating denture liners for the compositions have a glass transition temperature lower than the lower of an ambient temperature at which the liner is applied and a temperature inside the oral cavity. Phthalate-free embodiments, as well as kits are also described.

96 Claims, 4 Drawing Sheets

DENTURE LINER, DENTURE LINER KIT AND METHOD FOR MAKING A DENTURE LINER

FIELD OF THE INVENTION

This invention relates to dental compositions based on blends of particular polymer, plasticizer, and adhesive constituents, and to the process of making such compositions. The compositions are useful in prosthodontics, including formulating denture liners which have a glass transition temperature lower than the lower of an ambient temperature at which the liner is applied and a temperature inside the oral cavity. The most preferred embodiments are phthalate free. The invention further relates to denture liner kits.

BACKGROUND OF THE INVENTION

When a denture is worn for a long period of time, the fit between the denture and the alveolar ridge worsens. The shape of the gums changes with time as the gums recede. Since the denture is made from a hard material, it is incapable of adjusting to the change in shape of the gums. Thus, gaps begin to form between the denture and the gums. This can lead not only to the loosening of the denture, but also to an ulcer and/or inflammation due to uneven pressure exerted by the denture.

To alleviate these problems, it is necessary to provide a liner between the denture and the gum, which can both fill in the gaps that form between the denture and the gum and prevent damage to the gum. This liner may be flexible and plastically deformable, and may be capable of being used for a period of, for example, one week to a few weeks.

Numerous denture liners have been proposed to provide both comfort and better fit for the denture. Many of such liners achieve this goal by being soft, allowing them to conform to the shape of both the gums and the denture.

Conventionally, a soft denture liner is made of a synthetic resin in the form of powder, paste or a soft plate. Each time a user needs to apply a denture to the gum, the user takes the required amount of a denture base stabilizing material from a receptacle in the case of a powder or paste, or shapes it in an appropriate size and configuration in the case of a soft sheet. Conventional soft denture liners include various polymers, such as polyethylene, polypropylene, polybutene, polyvinyl chloride, ethylene-vinylacetate copolymer, nylon, polyvinyl fluoride, Teflon, polyacrylonitrile and polyvinyl alcohol.

Several soft denture liners have been disclosed, which are based on plasticized polyethyl methacrylate (PEMA). One such denture liner is disclosed in U.S. Pat. No. 5,061,182 to Kubo et al. (herein incorporated by reference). The patent discloses a denture base stabilizing sheet having a trapezoidal configuration, which is manufactured using a specific composition of PEMA, butyl phthalyl butyl glycolate (BPBG), and triacetin.

Soft liners mainly consisting of polymers of higher methacrylates, e.g., polyethylmethacrylate, a solvent, e.g., ethyl alcohol, and a plasticizer, e.g. butylphthalyl butylglycolate have also been described. These and others are disclosed in Graham et al, *J., Prosthetic Dentistry*, Volume 2, No. 4, pp. 422-8 (1989). The solvent and plasticizer are mixed with the polymer immediately prior to use, and the mixture is then applied to the surface of the denture. Swelling of the polymer by the solvent, and diffusion of the plasticizer into the polymer matrix cause the polymer to become soft and resilient.

U.S. Pat. No. 5,075,107 to Katakura (herein incorporated by reference) discloses a denture liner, which specifically excludes ethyl alcohol. This liner comprises a powdery component consisting of (a) either one of a copolymer of butyl methacrylate with ethyl methacrylate and a mixture of poly butyl methacrylate (PBMA) with PEMA and (b) a liquid component consisting of at least one of BPBG without ethanol, dibutyl phthalate (DBP), benzyl butyl phthalate, benzyl benzoate, ethyl benzoate, butyl benzoate and amyl benzoate, with the powdery and liquid components being mixed or kneaded together for use.

Another denture liner based on plasticized PEMA is disclosed in U.S. Pat. No. 5,436,283 to Okada et al. (herein incorporated by reference). The patent discloses a denture base lining material comprising a phthalic ester-based plasticizer containing ethyl alcohol and a powder component consisting of PEMA with or without a specific acrylate copolymer.

U.S. Pat. No. 5,513,988 relates to a known elastomeric methyl methacrylate-free soft material used as a denture reline material. The material includes powder and liquid components mixed together and cured, then used in denture applications. Where the invention involves lining over a void in an acrylic denture, the resultant mixture is applied over the underlying surface of the acrylic over the void to chemically and mechanically bond the mixture in a seamless bond to the underlying surface of acrylic. A known sealer component is then applied over the liner to create a non-absorbent exterior surface seal and glaze.

While the above conventional denture liners can provide some of the much needed relief for denture wearers, these liners have a number of problems. Conventional denture liners include polymeric materials, such as PEMA, which are chemically similar to the materials from which dentures are formed. These types of material allow the liner to be flexible and to be able to adjust to the changing shape of the gums. However, the liners tend to chemically bond to the denture, especially when the plasticizers are liberated over time. Thus, the liners become extremely difficult to separate from the denture. This is especially true with the materials discussed in U.S. Pat. No. 5,513,988 which promote chemical and mechanical bonding between the liner and the denture. Conversely, the instant invention promotes formation of adhesive bonding by providing a denture lining material which has a low glass transition temperature and can be characterized as resilient, as well as sticky or tacky.

Also, conventional denture liners do not have mucoadhesive properties. Therefore, they rely on either physically fitting the denture to the gum or on an additional adhesive. Such an approach, however, is deficient in that it leads to an inadequate hold or requires addition of a separate layer or layers of adhesives, which may interfere with the function of the liner and result in discomfort for the user.

The above-mentioned U.S. Pat. No. 5,436,283 attempts to solve the problem associated with separating the liner from the denture by including liquid paraffin and/or squalane in the composition of the liner. While such a modification helps to peel the liner from the denture, liquid paraffin and squalane also decrease the adhesion of the liner to the gum, which can lead to denture slippage.

Also problematic is the inclusion of phthalates in the plasticizer component of state-of-the art denture liners. Various advocacy groups are complaining that animal studies suggest that phthalates cause damage to an animal's internal organs such as kidneys, liver, lungs, and the reproductive system, including the testes. Since dentures and denture liners are worn in the mouth of the user where ingestion of phthalates may occur, it is desirable to produce a composition which is phthalate-free.

Accordingly, there is a need for a soft denture liner, which can provide sufficient comfort for the user and improve adhesion to the gums, while easing the process for separating the liner from the denture at the time the liner is replaced. Moreover, there is a need for a phthalate-free denture liner. Such needs are obtainable by providing denture liner compositions having a glass transition temperature lower than the lower of an ambient temperature at which the liner is applied and a temperature inside the oral cavity as described below.

SUMMARY OF THE INVENTION

Accordingly, it is an object of the present invention to provide a denture liner having both an improved adhesive action to form stronger and more lasting bonds between the denture and the oral cavity and an improved separability from the denture.

It is another object of the present invention to provide an improved denture liner, which can be readily applied and removed.

It is another object of the present invention to provide a denture liner which adjusts denture alignment to conform to user's gums in order to ensure an optimal fit.

It is another object of the present invention to provide a denture liner which is sufficiently soft to conform to the shape of the denture and the shape of the gum.

It is an object of the present invention to provide a denture liner which is phthalate-free.

It is an object of the present invention to reduce the possibility of a denture user from ingesting phthalates.

It is another object of the present invention to provide a denture liner which is sufficiently resilient and durable.

It is another object of the present invention to provide a denture liner which minimizes chemical and mechanical bond formation between the denture liner composition and the denture, such that the denture liner can be easily removed from the denture once applied.

It is another object of the present invention to provide a denture liner composition capable of being extruded thermoplastically.

It is another object of the present invention to provide a denture liner composition characterized as a mucoadhesive.

It is an object of the present invention to provide kits to facilitate making the denture liner compositions.

It is an object of the present invention to provide methods for producing denture liner compositions comprising combining the polymer component, the plasticizer component and the adhesive component to form the liner, which has a glass transition temperature that is lower than the lower of the ambient temperature at which the liner is applied and the temperature inside an oral cavity.

These and other objectives of the present invention are met by providing denture liners compositions and specifically those compositions which have a glass transition temperature lower than the lower of an ambient temperature at which the liner is applied and a temperature inside the oral cavity. Such liner characteristics provide soft denture liner compositions, which provide sufficient comfort for the user and improved adhesion to the gums, while easing the process for separating the liner from the denture at the time the liner is replaced.

These and other objectives of the present invention are achieved by providing a denture liner composition having a hydrophobic polymer component, comprising at least one polymer constituent; a plasticizer component comprising at least one plasticizer constituent capable of plasticizing the polymer component; and an adhesive component comprising at least one hydrophilic adhesive agent. Preferably, the denture liner has a glass transition temperature that is lower than the lower of an ambient temperature at which the liner is applied and a temperature inside an oral cavity. Preferably, the denture liner has at least one polymer constituent which is a thermoplastically extrudable polymer.

In one preferred embodiment the polymer constituent is hydrophobic acetate, acrylate ester derivative, and combinations thereof. Such hydrophobic acetates include polyvinyl acetate, polybutene, silicone, rubber, paraffin wax, and combinations thereof. Such acrylate ester derivatives include polyethyl methacrylate, polymethyl methacrylate, organosoluble cellulose, and combinations thereof. Most preferably the polymer constituent comprises two constituents, i.e. polyethyl methacrylate and polyvinyl acetate.

In one preferred embodiments the plasticizer constituent is phthalic acid derivative, glycerol triacetate, citric acid derivative, phosphoric acid derivative, ester of vegetable oil, glycol, glycol derivative, paraffin wax, a pentaerythritol ester of a fatty acid, stearic acid derivative, glycerol monostearate, polyethylene glycol, butyl phthalyl butyl glycolate, and combinations thereof. Such phthalic acid derivatives include butyl phthalyl butyl glycolate, dimethyl phthalate, dibutyl phthalate, and combinations thereof. Moreover, the glycerol triacetate may be triacetin. Suitable citric acid derivatives include triethyl citrate, acetyl triethyl citrate, acetyl tributyl citrate, and combinations thereof. Moreover, the phosphoric acid derivative may be triphenyl phosphate. Preferably the glycol derivative is diethylene glycol. Preferably the ester of vegetable oils includes caprylic triglyceride, capric triglyceride, propylene glycol di-caprylate/caprate, and combinations thereof. In one embodiment, the plasticizer is preferably two constituents, glyceryl triacetate and butyl phthalyl butyl glycolate.

In some embodiments the adhesive agent is preferably a natural gum, synthetic polymeric gum, synthetic polymer, mucoadhesive polymer, saccharide derivative, cellulose derivative, and combinations of these. The adhesive component may contain various adhesive constituents such as karaya gum, guar gum, gelatin, algin, alginate, tragacanth, chitosan, polyethylene glycol, acrylamide polymer, carbopol, polyvinyl alcohol, polyamine, polyquarternary compound, polybutene, silicone, polyethylene oxide, polyvinylpyrrolidone, cationic polyacrylamide polymer, and combinations thereof. In such embodiments, the adhesive component may further comprise at least one agent such as sodium carboxymethylcellulose, hydroxypropyl methylcellulose, hydroxyethyl methylcellulose, hydroxypropyl cellulose, hydroxyethyl cellulose, and combinations thereof. Most preferably the adhesive component comprises a mixture of sodium carboxymethylcellulose and polyethylene oxide.

In some preferred embodiments the denture liners have a polymer component which comprises of from about 5% to about 40% by weight of the total weight of the denture liner composition. Preferably the polymer component is between about 15% to about 25% by weight of the total weight of the denture liner composition.

In some preferred embodiments the denture liners have a plasticizer component comprising of from about 5% to about 55% by weight of the total weight of the denture liner composition. Preferably the plasticizer component comprises of from about 30% to about 55% by weight of the denture liner. Most preferably, the plasticizer component comprises about 50% by weight of the denture liner.

In some preferred embodiments the adhesive component of the denture liner comprises of from about 0.5% to about 35% by weight of the total weight of the denture liner composition. Preferably between about 20% to about 35% by weight of the denture liner. Most preferably the adhesive component comprises about 30% by weight of the denture liner.

Preferably the denture liner mix originally comprises ethanol which comprises of from about 1% to about 10% by weight of the initial denture liner components.

Some preferred denture liner embodiments comprise a hydrophobic polymer component, comprising at least one polymer constituent, wherein the polymer constituent comprises of from about 5% to about 40% by weight of the composition, and wherein the polymer constituent is selected from the group consisting of esterified copolymer of methyl vinyl ether and maleic anhydride, polyvinyl acetate, polyethyl methacrylate, and combinations thereof; a plasticizer component comprising at least one plasticizer constituent capable of plasticizing the polymer component, wherein the plasticizer constituent comprises of from about 5% to about 55% by weight of the composition, and wherein the plasticizer component is selected from the group consisting triacetin, butyl phthalyl butyl glycolate, caprylic triglyceride, capric triglyceride, propylene glycol di-caprylate/caprate and combinations thereof; an adhesive component comprising at least one hydrophilic adhesive agent, wherein the adhesive component comprises of from about 0.5% to about 35% by weight of the composition, and wherein the adhesive component is selected from the group consisting sodium carboxymethylcellulose, polyethylene oxide, and combinations thereof. Most preferably, the denture liner composition has a glass transition temperature that is lower than the lower of an ambient temperature at which the liner is applied and a temperature inside an oral cavity. Preferably such denture liner embodiments further comprise ethanol, wherein the ethanol comprises of from about 1% to about 10% by weight of the denture liner composition.

Some preferred denture liner embodiments comprise a hydrophobic polymer component, comprising at least one polymer constituent, wherein the polymer constituent comprises of from about 5% to about 40% by weight of the composition, and wherein the polymer component is selected from the group consisting of polyvinyl acetate, esterified copolymer of methyl vinyl ether and maleic anhydride, polybutene, silicone, rubber, paraffin wax, organosoluble cellulose, polyethyl methacrylate, polymethyl methacrylate, and combinations thereof; a plasticizer component comprising at least one plasticizer constituent capable of plasticizing the polymer component, wherein the plasticizer constituent comprises of from about 5% to about 55% by weight of the composition, and wherein the plasticizer component is selected from the group consisting of phthalic acid derivative, glycerol triacetate, citric acid derivative, phosphoric acid derivative, glycol, glycol derivative, paraffin wax, a pentaerythritol ester of a fatty acid, stearic acid derivative, glycerol monostearate, polyethylene glycol, butyl phthalyl butyl glycolate, butyl phthalyl butyl glycolate, dimethyl phthalate, dibutyl phthalate, triacetin, triethyl citrate, acetyl triethyl citrate, acetyl tributyl citrate, triphenyl phosphate, diethylene glycol, caprylic triglyceride, capric triglyceride, propylene glycol di-caprylate/caprate and combinations thereof; an adhesive component comprising at least one hydrophilic adhesive agent, wherein the adhesive component comprises of from about 0.5% to about 35% by weight of the composition, and wherein the adhesive component is selected from the group consisting of natural gum, synthetic polymeric gum, synthetic polymer, mucoadhesive polymer, saccharide derivative, cellulose derivative, karaya gum, guar gum, gelatin, algin, alginate, tragacanth, chitosan, polyethylene glycol, acrylamide polymer, carbopol, polyvinyl alcohol, polyamine, polyquarternary compound, polybutene, silicone, polyethylene oxide, polyvinylpyrrolidone, cationic polyacrylamide polymer, sodium carboxymethylcellulose, hydroxypropyl methylcellulose, hydroxyethyl methylcellulose, hydroxypropyl cellulose, hydroxyethyl cellulose, sodium carboxymethylcellulose, polyethylene oxide, and combinations thereof. Preferably the denture liner composition has a glass transition temperature that is lower than the lower of an ambient temperature at which the liner is applied and a temperature inside an oral cavity. Preferably such embodiments further comprise ethanol, wherein the ethanol comprises of from about 1% to about 10% by weight of the initial denture liner components when mixed together.

In some preferred embodiments of the present invention uses all of the same ingredients, excipients, and/or constituents as listed herein except that the embodiments are devoid of phthalate. Accordingly it is best characterized as phthalate-free. Such compositions are suitable for use with the kits and methods as described herein.

The objects of the present invention are achieved by providing denture liner kits comprising a container comprising at least a first compartment and a second compartment; wherein the first compartment contains a solid phase composition, wherein the second compartment contains a liquid phase composition, and wherein the solid phase composition and the liquid composition independently comprise at least one of: a hydrophobic polymer component comprising at least one thermoplastically extrudable hydrophobic polymer; a plasticizer component comprising at least one plasticizer constituent capable of plasticizing the polymer; and an adhesive component comprising at least one hydrophilic adhesive agent, wherein when the solid phase composition and liquid phase composition are combined, a composition is produced having a glass transition temperature that is lower than the lower of an ambient temperature at which the liner is applied and a temperature inside an oral cavity. Preferably the polymer components of such kits comprise polyethyl methacrylate and polyvinyl acetate. Most preferably the polymer component is polyethyl methacrylate. In some preferred embodiments the polymer component comprises a constituent selected from the group consisting of esterified copolymer of methyl vinyl ether and maleic anhydride, hydrophobic acetate, acrylate ester derivative, and combinations thereof. In some preferred embodiments the hydrophobic acetate is selected from the group consisting of polyvinyl acetate, polybutene, silicone, rubber, paraffin wax, and combinations thereof. Preferably, the acrylate ester derivative is selected from the group consisting of polyethyl methacrylate, polymethyl methacrylate, organosoluble cellulose, and combinations thereof.

In some embodiments the plasticizer constituent is selected from the group consisting of phthalic acid derivative, glyceryl triacetate, a citric acid derivative, a phosphoric acid derivative, glycol, a glycol derivative, paraffin wax, pentaerythritol ester of a fatty acid, stearic acid derivative, glycerol monostearate and polyethylene glycol. Preferably the plasticizer constituent is selected from the group consisting of glyceryl triacetate, butyl phthalyl butyl glycolate, caprylic triglyceride, capric triglyceride, propylene glycol di-caprylate/caprate and combinations thereof.

In some preferred kit embodiments the adhesive agent is selected from the group consisting of natural gum, synthetic polymeric gum, synthetic polymer, mucoadhesive polymer, saccharide derivatives, cellulose derivative, and combinations thereof. Preferably the adhesive agent is selected from the group consisting of karaya gum, guar gum, gelatin, algin, alginate, tragacanth, chitosan, polyethylene glycol, acrylamide polymer, carbopol, polyvinyl alcohol, polyamine, polyquarternary compound, polybutene, silicone, polyethylene oxide, polyvinylpyrrolidone, cationic polyacrylamide polymer, and combinations thereof. Preferably, the adhesive agent is selected from the group consisting of sodium carboxymethylcellulose, hydroxypropyl methylcellulose, hydroxyethyl methylcellulose, hydroxypropyl cellulose, hydroxyethyl cellulose, and combinations thereof. In some embodiments the adhesive agent is selected from the group consisting of sodium carboxymethylcellulose and polyethylene oxide, and combinations thereof.

In some kit embodiments the polymer component comprises of from about 5% to about 40% by weight of the denture liner composition, preferably between of from about 15% to about 25% by weight of the denture liner composition. Most preferably, the plasticizer component comprises of from about 5% to about 55% by weight of the denture liner composition.

In some kit embodiments the plasticizer component comprises of from about 30% to about 55% by weight of the denture liner composition. Preferably, the plasticizer component comprises about 50% by weight of the denture liner composition.

In some preferred kit embodiments, the adhesive component comprises of from about 0.5% to about 35% by weight of the denture liner composition. Preferably the adhesive component comprises of from about 20% to about 35% by weight of the denture liner composition. Most preferably, the adhesive component comprises about 30% by weight of the denture liner composition.

In some preferred embodiments, the denture liner kit further comprises ethanol. Preferably, the ethanol comprises of from about 1% to about 10% by weight of the liquid component.

The denture liner kit embodiments may further comprise a stir rod, emery board, glass bottle, cutting implement such as scissors or razor, and/or mixing tray or boat.

The objectives of the present invention are still further achieved by providing a method for making a denture liner comprising the steps of: providing denture liner components comprising: a hydrophobic polymer component comprising at least one thermoplastically extrudable hydrophobic polymer; a plasticizer component comprising at least one plasticizer capable of plasticizing the polymer; and an adhesive component comprising at least one hydrophilic adhesive agent; combining the denture liner components to form the denture liner having a glass transition temperature that is lower than the lower of an ambient temperature at which the liner is applied and a temperature inside an oral cavity. Preferably, the method further comprises the step of thermoplastically extruding the combined denture liner components. Preferably, in some embodiments the method further comprises the step of pressing and shaping the combined denture liner components. In some embodiments, the method preferably further comprises the hydrophobic polymer component comprising at least one polymer constituent, wherein the polymer constituent comprises of from about 5% to about 40% by weight of the composition, and wherein the polymer constituent is selected from the group consisting of polyvinyl acetate, esterified copolymer of methyl vinyl ether and maleic anhydride, polyethyl methacrylate, and combinations thereof, wherein the plasticizer component comprises at least one plasticizer constituent capable of solidifying the polymer component, wherein the plasticizer constituent comprises of from about 5 to about 55% by weight of the composition, and wherein the plasticizer component is selected from the group consisting triacetin, butyl phthalyl butyl glycolate, caprylic triglyceride, capric triglyceride, propylene glycol di-caprylate/caprate and combinations thereof, wherein the adhesive component comprises at least one hydrophilic adhesive agent, wherein the adhesive component comprises of from about 0.5% to about 35% by weight of the composition, and wherein the adhesive component is selected from the group consisting of sodium carboxymethylcellulose, polyethylene oxide, and combinations thereof. In some preferred embodiments the method further includes adding ethanol to the polymer starting materials.

As used herein the term "glass transition temperature" means the temperature at which the amorphous domains of a polymer take on the characteristic properties of the glass state-brittleness, stiffness, and rigidity. The term further means the temperature at which cured resins undergo a change from a glassy state to a softer more rubbery state. Moreover the term refers to, among other things, the approximate midpoint of the temperature range over which the glass transition takes place.

As used herein the term "ambient temperature" means the temperature of a medium surrounding an object. The term further refers to the temperature, usually of the air, that surrounds the denture liner. The term further relates to the temperature of a medium, such as gas or liquid, which comes into contact with or surrounds an apparatus such as a denture liner. Ambient temperature is normally defined as the nominal temperature of the air (or other gases, liquids, etc.) that surrounds the component, module, assembly, or system. The term includes but is not limited to room temperature as 23° C.±2° C. (73.4° F.±3.6° F.).

As used herein the term "thermoplastically extrudable polymer" refers to polymers which are capable of softening or fusing when heated and of hardening again when cooled which may further be shaped. Such polymers may further be shaped by forcing through a die.

As used herein the term "phthalate" means any phthalate including phthalate diesters. The term also refers to phthalic acid derivatives such as dimethyl phthalate, dibutyl phthalate, and butyl phthalyl butyl glycolate. The term also refers to branched alcohol phthalates such as dipropyl phthalate (DPP), diisobutyl phthalate (DIBP), diisohexyl phthalate (DIHP), diisoheptyl phthalate (DIHP), di(2-ethylhexyl) phthalate (DEHP/DOP), diisooctyl phthalate (DIOP), diisononyl phthalate (DINP), diisodecyl phthalate (DIDP), dipropylheptyl phthalate (DPHP), diundecyl phthalate (DUP), diisoundecyl phthalate (DIUP), and ditridecyl phthalate (DTDP/DITP). The term also refers to any mixed alcohol phthalates such as butylbenzyl phthalate (BBP), seven-nine phthalate (79P), nine-eleven phthalate (911P). The term also refers to any linear alcohol phthalate such as dimethyl phthalate (DMP), diethyl phthalate (DEP), di-n-butyl phthalate (DBP), six-ten phthalate (610P), eight-ten phthalate (810P), ten-twelve phthalate (1012P).

As used herein the term "phthalate-free" means that the composition does not contain any phthalate including phthalate diesters.

As used herein the term "percentage by weight" or "weight %" or "% weight", or "wt. %" means percentage by weight of a given material of the total weight of a mixture or composition.

As used herein the term "contacting" means the act of touching together, which includes, but is not limited to mixing.

DETAILED DESCRIPTION

Figure 1:
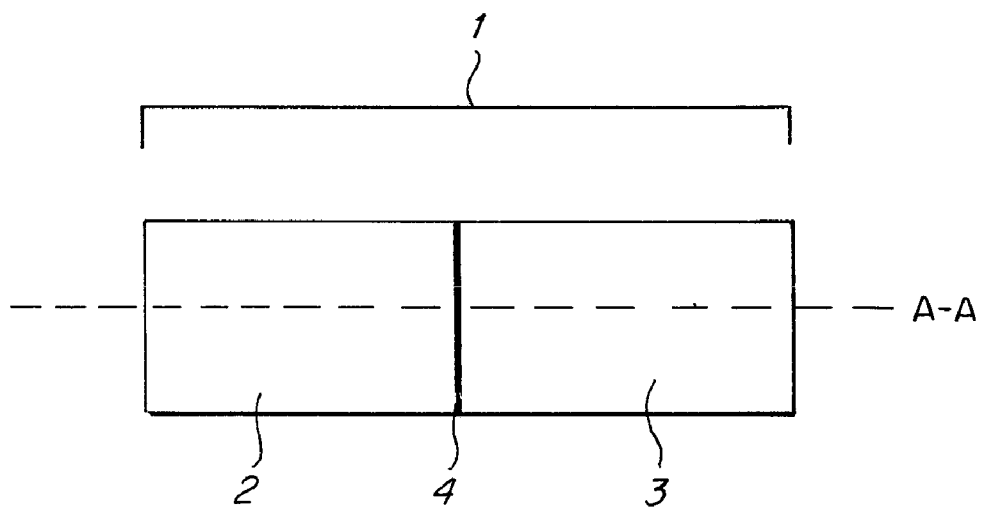
FIG. 1 is a top plan view of the denture liner kit in accordance with the present invention.

A denture liner according to the present invention has many different functions. It can, for example, serve as a cushion for the denture and provide comfort to the denture wearer. It can fill in the gaps formed by receding gums, so that the denture wearer does not have to get the dentures adjusted every time the shape of the gums changes. It also can act as a denture adhesive without the use of additional adhesive layers. Importantly, the denture liner of the present invention can be much more easily separated from denture than the conventional denture liners. Therefore, the denture wearer can avoid both purchasing additional denture adhesives and getting the dentures adjusted by the dentist by using a denture liner according to the present invention. Such results are obtainable by providing denture liner compositions that have a glass transition temperature lower than the lower of an ambient temperature at which the liner is applied and a temperature inside the oral cavity. Preferably the glass transition temperature for these compositions range between −55° C. to 26° C. More preferably, the glass transition temperature is in the range of −55° C. to 0° C. Most preferably, the glass transition temperature is between −55° C. to −70° C.

The denture liner of the present invention includes a polymer component comprising at least one thermoplastically extrudable hydrophobic polymer. To provide the necessary plasticity, the liner also includes a plasticizer compatible with the polymer. In order to provide the liner with mucoadhesive characteristics and to allow the liner to be removed from the denture, the liner also includes at least one hydrophilic adhesive agent, which is capable of adhering to the oral cavity. This adhesive agent makes the liner less hydrophobic, which weakens the bond between the polymer in the liner and the polymer of the denture.

The ingredients in the denture liner are combined in amounts that allow the liner to be sufficiently soft to conform to the shape of the denture and the shape of the gum. In fact, the liner may be sufficiently flowable to allow it to be applied from a tube. The liner is preferably sufficiently coherent and does not ooze out from under the denture.

The denture liner of the present invention, when extruded thermoplastically, cures and sets as a result of the action of the plasticizer component. This makes the denture fit to the gums, so that the action of saliva creates a bond in the manner of a water glass sitting on a paper coaster. The adhesives strengthen this bond.

Polymer Component

The denture liner of the present invention can comprise one or more hydrophobic polymers, which can serve as a hydrophobic vehicle, film former, filler between gums and denture, and/or adhesive carrier. Any polymer constituent, which satisfies at least one of these characteristics and which can be extruded with a plasticizer and an adhesive agent to form a denture liner, as required by the present invention, can be used. Examples of polymer constituents that may be used in the present invention include hydrophobic acetates, such as polyvinyl acetate (PVA), polybutenes, silicones, rubbers, paraffin wax, esterified copolymer of methyl vinyl ether and maleic anhydride, hydrophobic acrylate ester derivatives, such as PEMA and polymethyl methacrylate (PMMA), organosoluble cellulose, etc. Preferred polymers include esterified copolymer of methyl vinyl ether and maleic anhydride, PEMA, and PVA. PEMA is the most preferred hydrophobic polymer in accordance with the present invention.

For the denture adhesive kit, however, it is preferable to combine PEMA and PVA because PVA can provide the denture liner with more flexibility, flow and reversibility, which can allow the liner to be more easily removed from the kit and spread onto the denture. This combination surprisingly shows improved tacking qualities.

Another suitable polymer constituent for use with the present invention is esterified copolymer of methyl vinyl ether and maleic anhydride. Such copolymer is available from a commercial supplier. For example, the ISP Corporation of Wayne, N.J. provides polymeric free acid form, anhydride form, mixed salt form, and half ester forms of lower alkyl vinyl ether maleic anhydride polymer under its "GANTREZ" trademark. The "GANTREZ ES Series" which relates specifically to monoethyl ester of poly[methyl vinyl ether/maleic acid] is particularly suitable for the present invention for it provides improved tacking ability of the liner to the denture over the state-of-the-art denture liners. The "GANTREZ ES Series" provides suitable polymer component of the present invention in the half ester form which is produced by opening up the anhydride in alcohol. The commercial supplier offers a range of copolymers with different alkyl chain lengths and molecular weights. Typically, the copolymers are supplied as 50% alcoholic solutions.

Preferably, 100% esterified copolymer of methyl vinyl ether and maleic anhydride is used as a polymer component. One of ordinary skill in the art would readily be able to obtain 100% esterified copolymer of methyl vinyl ether and maleic anhydride by reacting one part of anhydride (available from the supplier) with 2 parts alcohol. Suitable alcohols include methanol, ethanol, propanol, etc. Furthermore, diols, triols and related substances may also be used to make 100% esterified copolymer of methyl vinyl ether and maleic anhydride, however, use thereof is less preferred since the chances of achieving crosslinking with a neighboring copolymer increases.

In general, the hydrophobic polymer content of the denture liner composition may be of from about 5% to about 40% by weight of the denture liner composition, preferably from about 15 to about 25 weight %.

Plasticizer Component

Any plasticizer constituent compatible with the polymer in the polymer component may be used, so long as the resulting denture liner has a glass transition temperature that is lower than the lesser of the ambient temperature at which the liner is applied and the temperature inside the oral cavity of the denture wearer. It is preferable that the plasticizer is food grade or better. As with the polymer, two or more plasticizers can be included in the denture liner.

Examples of useful plasticizers constituents in the context of the present invention include phthalic acid derivatives, such as BPBG, dimethyl phthalate, dibutyl phthalate, etc., glycerol triacetate (triacetin), citric acid derivatives, such as triethyl citrate, etc., phosphoric acid derivatives, such as triphenyl phosphate, etc., glycol and glycol derivatives, such as diethylene glycol, triethylene glycol ester of fatty acids, etc., paraffin waxes, pentaerythritol esters of fatty acids, stearic acids derivatives, glycerol monostearate, polyethylene glycols, etc. The derivatives of these compounds include various esters. Most preferably vegetable oil including ester of vegetable oil selected from the group consisting of caprylic triglyceride, capric triglyceride, propylene glycol di-caprylate/caprate, and combinations thereof.

In some embodiments, triacetin and BPBG are preferred plasticizers. BPBG has a boiling point from about 210° C. to about 220° C. (5 mmHg) ($C_4H_4COOC_4H_4COCH_2COOC_4H_9$). Triacetin has a boiling point of 285EC. These plasticizers allow the liner to set with the passage of time, depending on the temperature and the amount of moisture in the mouth.

In general, the plasticizer content of the denture liner may be of from about 5% to about 55% by weight of the denture liner composition, preferably about 30 to about 55 weight %, most preferably about 49 weight %.

In phthalate-free embodiments, vegetable oils, and esters thereof such as caprylic triglyceride, capric triglyceride, propylene glycol di-caprylate/caprate, and combinations of these are preferable. Although not wishing to be bound by this disclosure, it is believed that the vegetable oils avoid stearic hindrance that may occur when large molecules are untangling, providing a denture liner with improved tacking qualities.

Adhesive Agent

The present invention may comprise at least one hydrophilic adhesive agent, which is capable of adhering to the oral cavity. Like the plasticizer, the adhesive agents used in the denture liner should be food grade or better. In addition to mucoadhesive properties, the adhesive agents can also act as, for example, a tackifier and/or a swelling agent.

Since the polymer and the plasticizer are both generally hydrophobic, the adhesive agent provides the liner with some hydrophilic characteristics, weakening the bond between the polymer in the liner and the polymer in the denture. Thus, the liner can be more easily separated from the denture by, for example, applying moisture.

Suitable adhesive constituents include water-soluble polymers having the property of bonding to the oral cavity upon exposure to moisture. Such adhesive materials should be food grade or better and include natural gums, synthetic polymeric gums, adhesive materials commonly employed in denture adhesives, synthetic polymers, mucoadhesive polymers, hydrophilic polymers, saccharide derivatives, cellulose derivatives, and mixtures thereof. Examples of such materials include karaya gum, guar gum, gelatin, algin, alginates, such as sodium alginate, tragacanth, chitosan, polyethylene glycol, acrylamide polymers, carbopol, polyvinyl alcohol, polyamines, polyquaternary compounds, polybutenes, silicones, ethylene oxide polymers, polyvinylpyrrolidone, cationic polyacrylamide polymers, saccharide derivatives, cellulose derivatives, such as carboxymethylcellulose, sodium carboxymethylcellulose (NaCMC), hydroxypropyl methylcellulose (HPMC), hydroxyethyl methylcellulose (HEMC), hydroxypropyl cellulose (HPC) and hydroxyethyl cellulose (HEC) and other synthetic gums or polymers. Preferred adhesive agents are NaCMC, polyethylene oxide (polyox) and mixtures thereof.

In general, the adhesive agent content of the denture liner may be of from about 0.5% to about 35 weight %, preferably from about 20 to about 35 weight %, and most preferably about 30 weight %.

Additional Ingredients

The denture liner according to the present invention can contain additional ingredients. These ingredients can improve the functionality of the liner and/or provide ancillary benefits to the denture wearer.

For example, ethyl alcohol can be added to the denture liner in order to improve its flowability for shaping and application of the denture liner, particularly in the denture liner kit as will be described below. Since the alcohol will quickly evaporate at the time when the denture is applied, the negative effects generally associated with its use in dental products are minimized and the denture liner can set and function unhampered by alcohols extra softening effects. The amount of the alcohol present in the denture liner composition is generally of from about 1% to about 10 weight % of the denture liner.

Additional ingredients, which can be used in the denture liner in accordance with the present invention, include therapeutically active agents suitable for treating individuals in need thereof. These agents include antimicrobial agents, such as iodine, sulfonamides, bisbiguanides, or phenolics, antibiotics such as tetracycline, neomycin, kanamycin, metronidazole, or clindamycin, anti-inflammatory agents, such as aspirin, acetaminophen, naproxen and its salts, ibuprofen, ketorolac, flurbiprofen, indomethacin, eugenol, or hydrocortisone, dental desensitizing agents, such as potassium nitrate, strontium chloride or sodium fluoride, anesthetic agents, such as lidocaine or benzocaine; anti-fungals, aromatics, such as camphor, eucalyptus oil, and aldehyde derivatives, such as benzaldehyde; insulin, steroids, and anti-neoplastics. Certain forms of therapy and combinations of these agents in the same delivery system may be useful in order to obtain an optimal effect.

Other suitable additional ingredients include colorants and preservatives, such as methyl and propyl parabens. The denture liner compositions of the present invention may also include one or more components, which provide flavor, flagrance, and/or sensation benefit. These components include natural or artificial sweetening agents, menthol, menthyl lactate, wintergreen oil, peppermint oil, spearmint oil, leaf alcohol, as well as coolants 3-1-menthoxypropane-1,2-diol and paramenthane carboxyamide agents, such as N-ethyl-p-menthane-3-carboxamide.

One preferred embodiment of the present invention provides a denture liner composition comprising a hydrophobic polymer component, a plasticizer component and an adhesive component. The resulting compositions are suitable for adhesive bonding to a denture or acrylic substrate. The polymer component comprises at least one polymer constituent, wherein the polymer constituent comprises of from about 5% to about 40% by weight of the composition, wherein the polymer constituent is selected from the group consisting of polyvinyl acetate, polyethyl methacrylate, and combinations thereof; a plasticizer component comprising at least one plasticizer constituent capable of plasticizing the polymer component, wherein the plasticizer constituent comprises of from about 5 to about 55% by weight of the composition, and wherein the plasticizer constituent is selected from the group consisting triacetin, butyl phthalyl butyl glycolate, caprylic triglyceride, capric triglyceride, propylene glycol di-caprylate/caprate and combinations thereof; an adhesive component comprising at least one hydrophilic adhesive agent, wherein the adhesive component comprises of from about 0.5% to about 35% by weight of the composition, and wherein the adhesive component is selected from the group consisting of sodium carboxymethylcellulose, polyethylene oxide, and combinations thereof. This embodiment may further use ethanol as an initial reactant, wherein the ethanol comprises of from about 1% to about 10% by weight of the denture liner composition. This embodiment is made by the process illustrated below, and is well suited for the kit embodiments of the present invention.

Another preferred embodiment of the present invention provides a denture liner composition comprising: a hydrophobic polymer component, comprising at least one polymer constituent, wherein the polymer constituent comprises of from about 5 to about 40% by weight of the composition, and wherein the polymer component is selected from the group consisting of polyvinyl acetate, polybutene, silicone, rubber, paraffin wax, organosoluble cellulose, polyethyl methacrylate, polymethyl methacrylate, and combinations thereof; a plasticizer component comprising at least one plasticizer constituent capable of plasticizing the polymer component, wherein the plasticizer constituent comprises of from about 5 to about 55% by weight of the composition, and wherein the plasticizer component is selected from the group consisting of phthalic acid derivative, glycerol triacetate, citric acid derivative, phosphoric acid derivative, glycol, glycol derivative, paraffin wax, a pentaerythritol ester of a fatty acid, stearic acid derivative, glycerol monostearate, polyethylene glycol, butyl phthalyl butyl glycolate, butyl phthalyl butyl glycolate, dimethyl phthalate, dibutyl phthalate, triacetin, triethyl citrate, acetyl triethyl citrate, acetyl tributyl citrate, triphenyl phosphate, diethylene glycol, caprylic triglyceride, capric triglyceride, propylene glycol di-caprylate/caprate and combinations thereof; an adhesive component comprising at least one hydrophilic adhesive agent, wherein the adhesive component comprises of from about 0.5% to about 35% by weight of the composition, and wherein the adhesive component is selected from the group consisting of natural gum, synthetic polymeric gum, synthetic polymer, mucoadhesive polymer, saccharide derivative, cellulose derivative, karaya gum, guar gum, gelatin, algin, alginate, tragacanth, chitosan, polyethylene glycol, acrylamide polymer, carbopol, polyvinyl alcohol, polyamine, polyquarternary compound, polybutene, silicone, polyethylene oxide, polyvinylpyrrolidone, cationic polyacrylamide polymer, sodium carboxymethylcellulose, hydroxypropyl methylcellulose, hydroxyethyl methylcellulose, hydroxypropyl cellulose, hydroxyethyl cellulose, sodium carboxymethylcellulose, polyethylene oxide, and combinations thereof. Therapeutically active agents as described herein may also be included as an initial reactant in order to provide benefits for patients in need of treatment. Colorants and additional materials may also be provided. This embodiment is suitable for kits as described herein, and made by the methods described below.

One preferred embodiment of the present invention uses all of the same ingredients, excipients, and/or constituents as listed above except that it is devoid of any phthalate. Accordingly it is best characterized as phthalate-free. Although applicant does not wish to be bound by this disclosure, it is believed at least by consumer advocacy groups that phthalates, which are typically added to many plasticizer components, may be detrimental to the health of humans and animals. Hence in order to promote a safer denture liner, as well as the marketing of products devoid of phthalate, it is desirable to make a denture liner which is phthalate-free.

Accordingly, phthalate-free embodiments comprise a hydrophobic polymer component having at least one polymer constituent; a plasticizer component having at least one plasticizer constituent capable of plasticizing the polymer component; and an adhesive component comprising at least one hydrophilic adhesive agent. Preferably, these embodiments have a glass transition temperature that is lower than the lower of an ambient temperature at which the liner is applied and a temperature inside an oral cavity. Optionally, the polymer constituent is a thermoplastically extrudable polymer. The polymer constituent may similarly be a hydrophobic acetate, acrylate ester derivative, and combinations of these, where the hydrophobic acetate is selected from the group consisting of polyvinyl acetate, polybutene, silicone, rubber, paraffin wax, and combinations of these. The acrylate ester derivative is selected from the group consisting of polyethyl methacrylate, polymethyl methacrylate, organosoluble cellulose, and combinations of these. Preferably, the polymer constituent is a combination of polyethyl methacrylate and polyvinyl acetate. Esterified copolymer of methyl vinyl ether and maleic anhydride is also a suitable polymer.

The phthalate-free embodiments use a plasticizer constituent selected from the group consisting of glycerol triacetate, citric acid derivative, phosphoric acid derivative, ester of vegetable oil, glycol, glycol derivative, paraffin wax, a pentaerythritol ester of a fatty acid, stearic acid derivative, glycerol monostearate, polyethylene glycol, and combinations thereof. One of ordinary skill in the art may use any plasticizer with these embodiments so long as the plasticizer is devoid of phthalic acid derivatives including those selected from the group consisting of butyl phthalyl butyl glycolate, dimethyl phthalate, dibutyl phthalate, and combinations thereof. Examples of suitable plasticizers include triacetin, triethyl citrate, acetyl triethyl citrate, acetyl tributyl citrate, triphenyl phosphate, diethylene glycol, caprylic triglyceride, capric triglyceride, propylene glycol di-caprylate/caprate, and combinations of these.

The phthalate-free embodiments may use any adhesive component that one of ordinary skill in the art would use to make a denture liner so long as it is devoid of phthalate. Suitable adhesive components include natural gum, synthetic polymeric gum, synthetic polymer, mucoadhesive polymer, saccharide derivative, cellulose derivative, and combinations thereof. Other suitable adhesive components include karaya gum, guar gum, gelatin, algin, alginate, tragacanth, chitosan, polyethylene glycol, acrylamide polymer, carbopol, polyvinyl alcohol, polyamine, polyquarternary compound, polybutene, silicone, polyethylene oxide, polyvinylpyrrolidone, cationic polyacrylamide polymer, and combinations thereof. Adhesive agents also include ingredients selected from the group consisting of sodium carboxymethylcellulose, hydroxypropyl methylcellulose, hydroxyethyl methylcellulose, hydroxypropyl cellulose, hydroxyethyl cellulose, and combinations thereof. Preferably, the adhesive agent includes sodium carboxymethylcellulose and polyethylene oxide.

Suitable phthalate-free embodiments comprise a polymer component which comprises of from about 5% to about 40% by weight of the denture liner, or optionally about 15% to about 25% by weight of the denture liner.

Suitable phthalate-free embodiments comprise a plasticizer component comprising of from about 5% to about 55% by weight of the denture liner, or optionally, of from about 30% to about 55% by weight of the denture liner. Preferably, the plasticizer component comprises about 50% by weight of the denture liner.

Suitable phthalate-free embodiments comprise an adhesive component comprising from about 0.5% to about 35% by weight of the denture liner, or optionally of from about 20% to about 35% by weight of the denture liner. Preferably the adhesive component comprises about 30% by weight of the total weight of the denture liner.

Suitable phthalate-free embodiments further comprising ethanol. Such embodiments may comprise of from about 1% to about 10% by weight of the denture liner components when originally mixed together.

Process for Producing Denture Liner

The denture liner in accordance with the present invention can be manufactured by combining and mixing liquid and solid components. The mixtures may then be thermoplastically extruded to form a film, which is then cut to form individual liners.

Specifically, thermoplastic extrusion can be carried out using various methods. The extruder can be a melt pump. The mixed, polymeric material is melted, and then the melted material is forced via the die into a sheet form.

Also, the extruded liner can be prepared using an injection molding method. In this method, all the components of the denture liner are blended together at room temperature (about 15° C. to 35° C.). The blended compositions are then poured into the twin screw extruder hopper chamber. The chamber is set at about 80° C. to about 100° C. The co-rotating screws further blend the mixtures at an increased temperature and pressure. The heated and blended mixtures may then be injection molded into a die, which is pre-shaped into the desired form of the liner.

Other techniques, such as casting, calendaring, coating and extrusion, or a combination of two or more of these techniques, could also be used. In addition, in one embodiment, the components of the denture liner are first mechanically softened by a ring roller, smoothed on a hydraulic press, and die-cut as desired into denture liner shapes or other desired shapes.

The extruded liners can be of from about 0.1 mm to about 1 mm thick, preferably from about 0.25 mm to about 0.5 mm. If the liner is thicker than about 1 mm, the denture wearer may experience discomfort. If, however, the denture liner is thinner than about 0.1 mm, both the adhesive and the lining properties of the denture liner may be negatively affected.

Denture Liner Kit

While, as discussed above, the denture liner according to the present invention can be thermoplastically extruded to form a sheet, which is then cut and packed for use, the denture liner according to the present invention can also be produced in a form of a kit. The kit preferably comprises a packet, which contains two compartments, each of which houses denture liner ingredients in different phases.

The ingredients in one of the compartments can be, for example, in the solid phase, while the ingredients in the other compartment can be in the liquid phase. These compartments are separated by a separator, which can be removed or breached in order to combine and mix all of the denture liner ingredients. Once the ingredients are combined inside the packet, the packet it ruptured and the contents applied to the denture. It is preferable to thoroughly mix ingredients before placing them on the denture.

Figure 2:
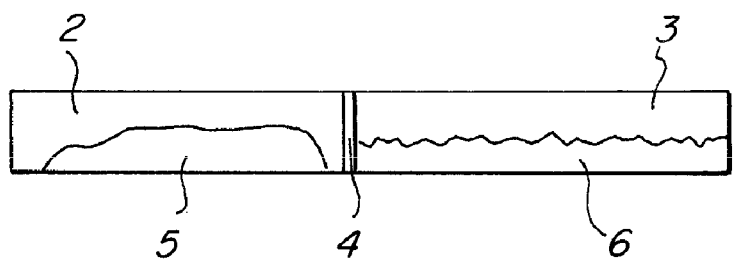
FIG. 2 is a cross-sectional view of the denture liner kit of FIG. 1, taken along line A-A.

An exemplary kit in accordance with the present invention is shown in FIGS. 1 and 2. This kit is in the form of a packet (1), which is similar to a ketchup packet or the like commonly available on the market. However, packet 1 contains at least a first compartment (2) and a second compartment (3) divided by a separator (4). As shown in FIG. 2, first compartment (2) contains solid phase powder components (5) and second compartment (3) contains liquid phase component (6). Separator (4) may be breached by squeezing one of the compartments, thus propelling its contents into the other compartment.

Solid (e.g., powder) components in accordance with the present invention can include the polymer component and the adhesive. The liquid component can include the plasticizers. However, it should be noted that there is no specific limitations as to which ingredient may be present in liquid or solid form in the kit. For example, some polymers, which are a part of the polymer component, may also be present in liquid form.

It is preferable that the denture liner components placed in the kit be in such proportions that the resulting mixture is sufficiently flowable to be spread on the denture. This can be achieved, for example, by including an additional amount of plasticizer or including alcohol in the composition. The addition of alcohol, which is placed in the compartment containing liquid ingredients, can provide the denture liner composition with flowability, ultimately evaporating to leave behind a denture liner, which has the desired properties.

Figure 3:
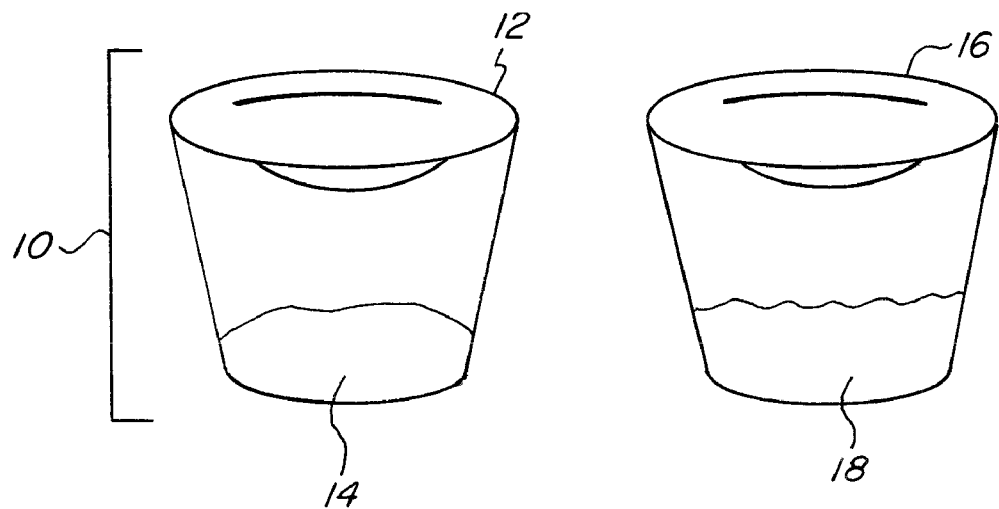
FIG. 3 is a front plan view of the denture liner kit in accordance with the present invention.

FIG. 3 shows denture liner kit (10) in accordance with the present invention. Kit (10) comprises first compartment (12) containing a predetermined amount of solid phase composition (14). Also shown is second compartment (16) containing a predetermined amount of liquid phase composition (18). First compartment (12) and second compartment (16) may be made out of any material known to one of ordinary skill in the art which is capable of containing a powder or a liquid, such as glass or preferably plastic. Also, first compartment (12) and second compartment (16) may further contain a cover (not shown in FIG. 3) for containing the solid and liquid phase compositions within the compartment. Aluminum foil is a suitable cover for the compartments for it facilitates use by being easily removable.

Figure 4:
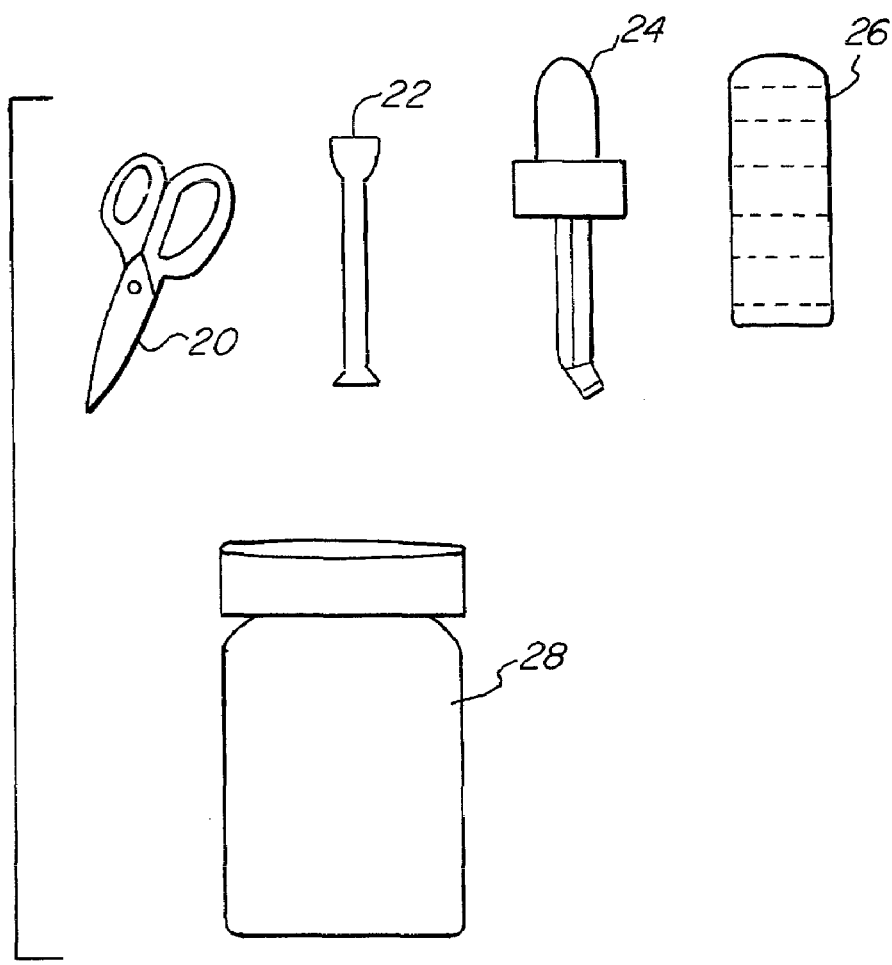
FIG. 4 is a front plan view of various components of the denture liner kit in accordance with the present invention.

Referring now to FIG. 4, various components of the denture liner kit in accordance with the present invention are shown. The various components may be optionally included with the kit to facilitate users on forming and shaping their denture liner. For example, cutting implement (20) is provided in order to help a user cut the resulting polymer composition to a particular shape. Cutting implement (20) may be a pair of scissors, razor blade, or the like. Stir rod (22) is provided to facilitate users in mixing the liquid composition and solid composition to uniformity. Stir rod (22) may be made out of any suitable material for mixing a powder and a liquid including but not limited to glass, plastic, or wood. Dropper (24) is also provided in order to help a user mix liquid composition with solid composition. Emery board (26) is provided to help a user contour the liner to a desired shape. Bottle (28) is shown as an alternative shape for second compartment, for any small plastic or glass bottle is suitable for holding liquid component.

Figure 5:
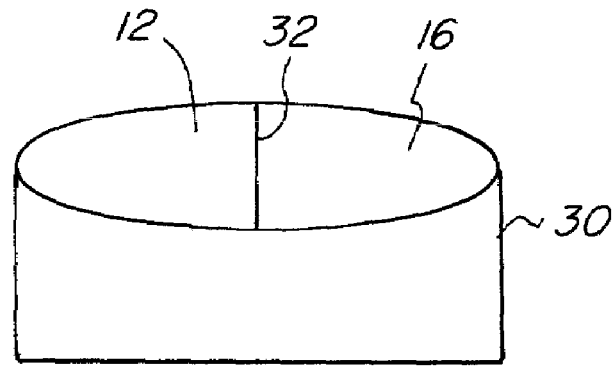
FIG. 5 is a front plan view of the denture liner kit in a single container in accordance with the present invention.

FIG. 5 shows a single container (30) where first compartment (12) and second compartment (16) are combined in one single container. Divider (32) is a wall between first compartment (12) and second compartment (16). Divider

(32) may be made out of an easily breakable material such as plastic or tin foil. When a user breaks the divider, the components of first compartment (12) and second compartment (16) mix together in a single container.

Figure 6:
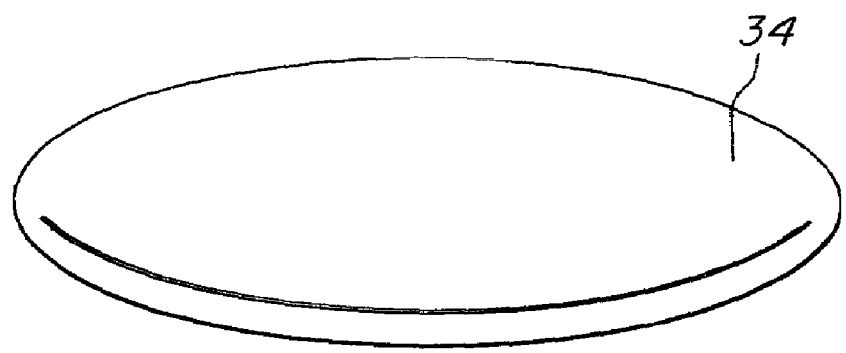
FIG. 6 is a side plan view of a mixing tray suitable for use with denture liner kit of the present invention.

The components of the present invention can also be easily mixed by supplying mixing tray such as shown in FIG. 6. User simply places the solid composition and liquid composition onto the tray (34) and mixes the components to a uniform composition.

The following are some non-limiting examples of denture liners in accordance with the present invention.

EXAMPLE 1

A denture liner was prepared by combining components in amount as listed in Table 1. This liner was made by blending all the components in a Hobart7 mixer. A pre weighed sample, which was approximately the size of a typical table tennis ball, was sandwiched between two release papers. Using a hydraulic Carver7 press, and a shim gap of 0.5 mm, the sample was compressed at 10 tons for 20 seconds. The compressed composition was then cut by hand to the shape of the denture liner.

TABLE 1

| Ingredient | Content (wt. %) |
| --- | --- |
| PEMA | 21 |
| Triacetin | 28 |
| BPBG (Morflex 190) | 21 |
| Polyox | 15 |
| NaCMC | 15 |

The polymer component of this denture liner is PEMA, which functions as a main film former, vehicle, gap filler and adhesive carrier. The plasticizer component consists of triacetin and BPBG. The adhesive component includes polyox and NaCMC. Specifically, polyox is a tackifier and a mucoadhesive. NaCMC is a swelling component and a mucoadhesive.

The denture liner of this example cures and sets as a result of the action of the plasticizers. This makes the denture fit to the gums, so that the action of saliva creates a bond in the manner of a water glass sitting on a paper coaster. The adhesives strengthen this bond.

Since this denture liner includes PEMA, the liner can easily adhere to the denture and prevent the denture from sliding off the liner. The presence of the two adhesive agents, which are the only hydrophilic components of this denture liner, allows the denture liner to be easily separated from the denture after use. Furthermore, the mucoadhesive properties of these adhesive agents allow the liner to more securely place the denture onto the gums without the need for an additional denture adhesive.

This denture liner can also be produced by first combining triacetin and BPBG, which are both in liquid form. Then, the PEMA, NaCMC and polyox powders are added to the liquid, and the resulting composition is thoroughly mixed to form a slurry. Once a slurry containing all components is prepared, it is thermoplastically extruded to form a thin film, which is then cut into individual pieces.

EXAMPLE 2

A denture liner is prepared by combining components in amounts as listed in Table 2 in the same manner as the liner in Example 1.

TABLE 2

| Ingredient | Content (wt. %) |
| --- | --- |
| PEMA | 35 |
| Triacetin | 17.5 |
| BPBG (Morflex 190) | 17.5 |
| Polyox | 15 |
| NaCMC | 15 |

This denture liner also contains a trace level of ethyl alcohol, which is added to make the material more flowable. The other components of this denture liner perform the same functions as in the liner of Example 1.

EXAMPLE 3

A denture liner kit is prepared by providing a packet with two compartments, as shown in FIG. 1. PEMA, NaCMC and polyox are placed in compartment 1 in powder form. PVA, triacetin and BPBG, which are in liquid form, are placed in compartment 2. The amounts of each of the ingredients in the kit are as listed in Table 3.

TABLE 3

| Ingredient | Content (wt. %) | Phase |
| --- | --- | --- |
| Triacetin | 28 | Liquid |
| BPBG | 21 | Liquid |
| PVA | 5 | Solid |
| PEMA | 16 | Solid |
| Polyox | 15 | Solid |
| NaCMC | 15 | Solid |

Once the separator 3 between compartment 1 and compartment 2 is breached, the components are mixed to form a denture liner composition. In this composition, each of the components performs the same functions as in the liner of Example 1. PVA, like PEMA, is used as a vehicle polymer, which adds flexibility, flow and reversibility to the denture liner.

EXAMPLE 4

An in vivo test was conducted to compare the holding and comfort ability of the denture liner of the composition of Example 1, as recited in Table 1. Human volunteers who had previously used dental adhesive creams were asked to compare this denture liner to the conventional Sea-Bond7 dental adhesive laminate in accordance with U.S. Pat. No. 4,632,080, which utilizes an adhesive combination of polyox and CMC, by using both products individually to secure dentures in their mouths. Some volunteers were given the denture liner in accordance with the present invention, while others were given the Sea Bond 7 denture adhesive. Each volunteer was asked to rate the hold of the denture on the scale from 1 to 10 (10 being the best) immediately after application and at 30 minutes after application, as well as at 1, 3 and 6 hours after application. The cumulative/average results of the comparative study are presented in Table 4.

TABLE 4

| Time | Denture Liner | Sea-Bond 7 |
| --- | --- | --- |
| Initial Assessment | 7.6 | 8.0 |
| 30 min. | 9.0 | 8.1 |
| 1 hr. | 9.4 | 7.8 |

TABLE 4-continued

| Time  | Denture Liner | Sea-Bond 7 |
|-------|---------------|------------|
| 4 hr. | 9.0           | 5.4        |
| 6 hr. | 9.1           | 5.2        |

As demonstrated in Table 4, the denture liner of the invention provides significantly improved bonding over time over the conventional denture adhesive, which utilizes at least the same adhesive components. This result was surprising in that the denture liner of the present invention was not expected to provide a better hold than the conventional denture adhesive. It is believed that the improved hold is the result of the synergy between the setting power of the hydrophilic components of the liner and the adhesive power of the hydrophilic adhesive component.

EXAMPLE 5

A denture liner kit is prepared by providing a packet with two compartments, as shown in FIG. 1. PEMA, NaCMC, polyox, and 100% esterfied Gantrez® are placed in compartment 1 in powder form. PVA, triacetin and vegetable oils, which are in liquid form, are placed in compartment 2. The amounts of each of the ingredients in the kit are as listed in Table 5.

TABLE 5

| Ingredient | Content (wt. %) | Phase |
|---|---|---|
| Triacetin | 28 | Liquid |
| Vegetable Oil | 21 | Liquid |
| PVA | 5 | Solid |
| PEMA | 16 | Solid |
| Polyox | 15 | Solid |
| NaCMC | 10 | Solid |
| esterified copolymer of methyl vinyl ether and maleic anhydride | 5 | Solid |

Table 5 shows an additional example of various embodiments of the present invention which are phthalate-free. Another similar example uses all of the same ingredients listed in Table 5 except the esterfied copolymer of methyl vinyl ether and maleic anhydride is absent and an additional 5% NaCMC is added in its place.

The denture liners have a glass transition temperature that is most preferably lower than the lower of an ambient temperature at which the liner is applied and a temperature inside an oral cavity (i.e. approximately 98.6 degrees F. (37 degrees C.)).

The glass transition temperature of a sample having the ingredients of Example 1 was measured using a DSC (differential scanning calorimetry). The glass transition temperature was found to be −63° C. A similar sample having PEMA, Triacetin, and BPBG was measured and the glass transition temperature of the material was found to be −70° C. The optimum and preferred Tg range for products of the present invention is between −55° C. to −70° C. However, workable results are obtainable for compositions having a Tg between −55° C. to 26° C.

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A denture liner composition comprising:
a blend of:
a hydrophobic polymer component, comprising at least two polymer constituents comprising a hydrophobic acetate and an acrylate ester derivative;
a plasticizer component comprising at least one plasticizer constituent capable of plasticizing the polymer component; and
an adhesive component comprising at least one hydrophilic adhesive agent.

2. The denture liner according to claim 1, wherein at least one polymer constituent of the at least two polymer constituents is a thermoplastically extrudable polymer.

3. The denture liner according to claim 1, wherein the polymer constituents further comprise an additional constituent selected from the group consisting of esterified copolymer of methyl vinyl ether and maleic anhydride, polybutene, silicone, rubber, paraffin wax, and combinations thereof.

4. The denture liner according to claim 1, wherein the hydrophobic acetate is polyvinyl acetate.

5. The denture liner according to claim 1, wherein the acrylate ester derivative is selected from the group consisting of polyethyl methacrylate, polymethyl methacrylate, and combinations thereof.

6. The denture liner according to claim 1, wherein the polymer constituents comprise polyethyl methacrylate and polyvinyl acetate.

7. The liner according to claim 1, wherein the plasticizer constituent is selected from the group consisting of phthalic acid derivative, glycerol triacetate, citric acid derivative, phosphoric acid derivative, vegetable oil, ester of vegetable oil, glycol, glycol derivative, paraffin wax, a pentaerythritol ester of a fatty acid, stearic acid derivative, glycerol monostearate, polyethylene glycol, butyl phthalyl butyl glycolate, and combinations thereof.

8. The denture liner according to claim 7, wherein the phthalic acid derivative is selected from the group consisting of butyl phthalyl butyl glycolate, dimethyl phthalate, dibutyl phthalate, and combinations thereof.

9. The denture liner according to claim 7, wherein the glycerol triacetate is triacetin.

10. The denture liner according to claim 7, wherein the citric acid derivative is triethyl citrate, acetyl triethyl citrate, acetyl tributyl citrate, and combinations thereof.

11. The denture liner according to claim 7, wherein the phosphoric acid derivative is triphenyl phosphate.

12. The denture liner according to claim 7, wherein the glycol derivative is diethylene glycol.

13. The denture liner according to claim 7, wherein the ester of vegetable oil is selected from the group consisting of caprylic triglyceride, capric triglyceride, propylene glycol di-caprylate/caprate, and combinations thereof.

14. The denture liner according to claim 1, wherein the plasticizer constituent comprises glyceryl triacetate and butyl phthalyl butyl glycolate.

15. The denture liner according to claim 1, wherein the adhesive agent is selected from the group consisting of natural gum, synthetic polymeric gum, synthetic polymer, mucoadhesive polymer, saccharide derivative, cellulose derivative, and combinations thereof.

16. The denture liner according to claim 1, wherein the adhesive component further comprises an adhesive constituent selected from the group consisting of karaya gum, guar gum, gelatin, algin, alginate, tragacanth, chitosan, polyethylene glycol, acrylamide polymer, carbopol, polyvinyl alcohol, polyamine, polyquarternary compound, polybutene, silicone, polyethylene oxide, polyvinylpyrrolidone, cationic polyacrylamide polymer, and combinations thereof.

17. The denture liner according to claim 1, wherein the adhesive agent is selected from the group consisting of sodium carboxymethylcellulose, hydroxypropyl methylcellulose, hydroxyethyl methylcellulose, hydroxypropyl cellulose, hydroxyethyl cellulose, and combinations thereof.

18. The denture liner according to claim 1, wherein the adhesive agent is sodium carboxymethylcellulose and polyethylene oxide.

19. The denture liner according to claim 1, wherein the polymer component comprises of from about 5% to about 40% by weight of the denture liner.

20. The denture liner according to claim 1, wherein the polymer component comprises of from about 15% to about 25% by weight of the denture liner.

21. The denture liner according to claim 1, wherein the plasticizer component comprises of from about 50% a to about 55% by weight of the denture liner.

22. The denture liner according to claim 1, wherein the plasticizer component comprises of from about 30% to about 55% by weight of the denture liner.

23. The denture liner according to claim 1, wherein the plasticizer component comprises about 50% by weight of the denture liner.

24. The denture liner according to claim 1, wherein the adhesive component comprises from about 0.5% to about 35% by weight of the denture liner.

25. The denture liner according to claim 1, wherein the adhesive component comprises of from about 20% to about 35% by weight of the denture liner.

26. The denture liner according to claim 1, wherein the adhesive component comprises about 30% by weight of the denture liner.

27. The denture liner according to claim 1, further comprising ethanol.

28. The denture liner according to claim 27, wherein the ethanol comprises of from about 1% to about 10% by weight of the denture liner.

29. The denture liner of claim 1 further comprising a therapeutic agent selected from the group consisting of iodine, sulfonamides, bisbiguanides, phenolics, tetracycline, neomycin, kanamycin, metronidazole, clindamycin, aspirin, acetaminophen, naproxen and pharmaceutically acceptable salts thereof, ibuprofen, ketorolac, flurbiprofen, indomethacin, eugenol, hydrocortisone, potassium nitrate, strontium chloride, sodium fluoride, lidocaine, benzocaine, camphor, eucalyptus oil, benzaldehyde, insulin, steroid, anti-neoplastics, and combinations thereof.

30. The denture liner of claim 1 further comprising a supplementary reagent selected from the group consisting of methyl parabens, propyl parabens, artificial sweetener, menthol, menthyl lactate, wintergreen oil, peppermint oil, spearmint oil, leaf alcohol, 3-1-menthoxypropane-1,2-diol, N-ethyl-p-menthane-3-carboxamide, and combinations thereof.

31. A denture liner kit comprising:
 a first compartment and a second compartment;
 wherein the first compartment contains a solid phase composition, wherein the second compartment contains a liquid phase composition, and wherein the solid phase composition and the liquid composition independently comprise at least one of:
 a hydrophobic polymer component comprising at least one thermoplastically extrudable hydrophobic polymer;
 a plasticizer component comprising at least one plasticizer constituent capable of plasticizing the polymer; and
 an adhesive component comprising at least one hydrophilic adhesive agent, wherein when the solid phase composition and liquid phase composition are combined, a composition is produced having a glass transition temperature that is lower than the lower of an ambient temperature at which the liner is applied and a temperature inside an oral cavity.

32. The denture liner kit according to claim 31, wherein the polymer component is selected from the group consisting of polyethyl methacrylate, esterified copolymer of methyl vinyl ether and maleic anhydride, polyvinyl acetate, polybutene, silicone, rubber, paraffin wax, and combinations thereof.

33. The denture liner kit according to claim 31, wherein the polymer component is polyethyl methacrylate.

34. The denture liner kit according to claim 31, wherein the polymer component comprises a constituent selected from the group consisting of hydrophobic acetate, acrylate ester derivative, and combinations thereof.

35. The denture liner kit according to claim 34, wherein the hydrophobic acetate is polyvinyl acetate.

36. The denture liner kit according to claim 34, wherein the acrylate ester derivative is selected from the group consisting of polyethyl methacrylate, polymethyl methacrylate, and combinations thereof.

37. The denture liner kit according to claim 31, wherein the plasticizer constituent is selected from the group consisting of phthalic acid derivative, glyceryl triacetate, a citric acid derivative, a phosphoric acid derivative, glycol, a glycol derivative, paraffin wax, pentaerythritol ester of a fatty acid, stearic acid derivative, glycerol monostearate and polyethylene glycol.

38. The denture liner kit according to claim 31, wherein the plasticizer constituent is selected from the group consisting of glyceryl triacetate, butyl phthalyl butyl glycolate, caprylic triglyceride, capric triglyceride, propylene glycol di-caprylate/caprate and combinations thereof.

39. The denture liner kit according to claim 31, wherein the adhesive agent is selected from the group consisting of natural gum, synthetic polymeric gum, synthetic polymer, mucoadhesive polymer, saccharide derivatives, cellulose derivative, and combinations thereof.

40. The denture liner kit according to claim 31, wherein the adhesive agent is selected from the group consisting of karaya gum, guar gum, gelatin, algin, alginate, tragacanth, chitosan, polyethylene glycol, acrylamide polymer, carbopol, polyvinyl alcohol, polyamine, polyquarternary compound, polybutene, silicone, polyethylene oxide, polyvinylpyrrolidone, cationic polyacrylamide polymer, and combinations thereof.

41. The denture liner kit according to claim 31 wherein the adhesive agent is selected from the group consisting of carboxymethylcellulose, sodium carboxymethylcellulose, hydroxypropyl methylcellulose, hydroxyethyl methylcellulose, hydroxypropyl cellulose, hydroxyethyl cellulose, and combinations thereof.

42. The denture liner kit according to claim 31, wherein the adhesive agent is selected from the group consisting of sodium carboxymethylcellulose, polyethylene oxide, and combinations thereof.

43. The denture liner kit according to claim 31, wherein the polymer component comprises of from about 5% to about 40% by weight of the denture liner composition.

44. The denture liner kit according to claim 31, wherein the polymer component comprises of from about 15% to about 25% by weight of the denture liner composition.

45. The denture liner kit according to claim 31, wherein the plasticizer component comprises of from about 5% to about 55% by weight of the denture liner composition.

46. The denture liner kit according to claim 31, wherein the plasticizer component comprises of from about 30% to about 55% by weight of the denture liner composition.

47. The denture liner kit according to claim 31, wherein the plasticizer component comprises about 50% by weight of the denture liner composition.

48. The denture liner kit according to claim 31, wherein the adhesive component comprises of from about 0.5% to about 35% by weight of the denture liner composition.

49. The denture liner kit according to claim 31, wherein the adhesive component comprises of from about 20% to about 35% by weight of the denture liner composition.

50. The denture liner kit according to claim 31, wherein the adhesive component comprises about 30% by weight of the denture liner composition.

51. The denture liner kit according to claim 31, further comprising ethanol.

52. The kit according to claim 51, wherein the ethanol comprises of from about 1% to about 10% by weight of the liquid component.

53. The denture liner kit according to claim 31 further comprising an emery board.

54. The denture liner kit according to claim 31 further comprising scissors.

55. The denture liner kit according to claim 31 further comprising a dropper.

56. The denture liner kit according to claim 31 wherein said first compartment is a mixing cup.

57. The denture liner kit according to claim 31 wherein said second compartment is a bottle.

58. The denture liner kit according to claim 31 wherein the first compartment and the second compartment are combined to form a single container.

59. The denture liner kit according to claim 31 further comprising a stir rod.

60. The denture liner kit according to claim 31 further comprising a mixing tray.

61. A method for making a denture liner comprising the steps of:
blending denture liner components comprising:
a hydrophobic polymer component comprising at least one hydrophobic polymer constituent comprising an acrylate ester derivative;
a plasticizer component comprising at least one plasticizer capable of plasticizing the polymer; and
an adhesive component comprising at least one hydrophilic adhesive agent; combining the denture liner components to form the denture liner.

62. The method according to claim 61, further comprising the step of thermoplastically extruding the contacted denture liner components.

63. The method according to claim 61, further comprising the step of pressing and shaping the combined denture liner components.

64. The method according to claim 61, further comprising adding ethanol.

65. A denture liner composition comprising:
a blend of:
a hydrophobic polymer component, comprising at least one polymer constituent comprising an acrylate ester derivative;
a plasticizer component comprising at least one plasticizer constituent capable of plasticizing the polymer component; and
an adhesive component comprising at least one hydrophilic adhesive agent.

66. The denture liner composition of claim 65 wherein the denture liner has a glass transition temperature that is lower than the lower of an ambient temperature at which the liner is applied and a temperature inside an oral cavity.

67. The denture liner according to claim 65, wherein at least one polymer constituent is a thermoplastically extrudable polymer.

68. The denture liner according to claim 65, wherein the polymer constituent further comprises an additional constituent selected from the group consisting of esterified copolymer of methyl vinyl ether and maleic anhydride, hydrophobic acetate, polybutene, silicone, rubber, paraffin wax, and combinations thereof.

69. The denture liner according to claim 68, wherein the hydrophobic acetate is polyvinyl acetate.

70. The denture liner according to claim 65, wherein the acrylate ester derivative is selected from the group consisting of polyethyl methacrylate, polymethyl methacrylate, and combinations thereof.

71. The denture liner according to claim 65, wherein the polymer constituent comprises polyethyl methacrylate and polyvinyl acetate.

72. The liner according to claim 65, wherein the plasticizer constituent is selected from the group consisting of vegetable oil, glycerol triacetate, citric acid derivative, phosphoric acid derivative, ester of vegetable oil, glycol, glycol derivative, paraffin wax, a pentaerythritol ester of a fatty acid, stearic acid derivative, glycerol monostearate, polyethylene glycol, and combinations thereof.

73. The denture liner according to claim 72, wherein the plasticizer is devoid of phthalic acid derivatives selected from the group consisting of butyl phthalyl butyl glycolate, dimethyl phthalate, dibutyl phthalate, and combinations thereof.

74. The denture liner according to claim 72, wherein the glycerol triacetate is triacetin.

75. The denture liner according to claim 72, wherein the citric acid derivative is triethyl citrate, acetyl triethyl citrate, acetyl tributyl citrate, and combinations thereof.

76. The denture liner according to claim 72, wherein the phosphoric acid derivative is triphenyl phosphate.

77. The denture liner according to claim 72, wherein the glycol derivative is diethylene glycol.

78. The denture liner according to claim 72, wherein the ester of vegetable oil is selected from the group consisting of caprylic triglyceride, capric triglyceride, propylene glycol di-caprylate/caprate, and combinations thereof.

79. The denture liner according to claim 65, wherein the adhesive agent is selected from the group consisting of natural gum, synthetic polymeric gum, synthetic polymer, mucoadhesive polymer, saccharide derivative, cellulose derivative, and combinations thereof.

80. The denture liner according to claim 65, wherein the adhesive component further comprises an adhesive constituent selected from the group consisting of karaya gum, guar gum, gelatin, algin, alginate, tragacanth, chitosan, polyethylene glycol, acrylamide polymer, carbopol, polyvinyl alcohol, polyamine, polyquarternary compound, polybutene, silicone, polyethylene oxide, polyvinylpyrrolidone, cationic polyacrylamide polymer, and combinations thereof.

81. The denture liner according to claim 65, wherein the adhesive agent is selected from the group consisting of sodium carboxymethylcellulose, hydroxypropyl methylcellulose, hydroxyethyl methylcellulose, hydroxypropyl cellulose, hydroxyethyl cellulose, and combinations thereof.

82. The denture liner according to claim 65, wherein the adhesive agent is sodium carboxymethylcellulose and polyethylene oxide.

83. The denture liner according to claim 65, wherein the polymer component comprises of from about 5% to about 40% by weight of the denture liner.

84. The denture liner according to claim 65, wherein the polymer component comprises of from about 15% to about 25% by weight of the denture liner.

85. The denture liner according to claim 65, wherein the plasticizer component comprises of from about 5% to about 55% by weight of the denture liner.

86. The denture liner according to claim 65, wherein the plasticizer component comprises of from about 30% to about 55% by weight of the denture liner.

87. The denture liner according to claim 65, wherein the plasticizer component comprises about 50% by weight of the denture liner.

88. The denture liner according to claim 65, wherein the adhesive component comprises from about 0.5% to about 35% by weight of the denture liner.

89. The denture liner according to claim 65, wherein the adhesive component comprises of from about 20% to about 35% by weight of the denture liner.

90. The denture liner according to claim 65, wherein the adhesive component comprises about 30% by weight of the denture liner.

91. The denture liner according to claim 65, further comprising ethanol.

92. The denture liner according to claim 91, wherein the ethanol comprises of from about 1% to about 10% by weight of the denture liner.

93. The method according to claim 61, wherein the polymer constituent further comprises an additional constituent is selected from the group consisting of esterified copolymer of methyl vinyl ether and maleic anhydride, hydrophobic acetate, polybutene, silicone, rubber, paraffin wax, and combinations thereof.

94. The method according to claim 61, wherein the polymer constituent comprises polyethyl methacrylate and polyvinyl acetate.

95. The method according to claim 61, wherein the plasticizer component comprising at least one plasticizer constituent capable of solidifying the polymer component is selected from the group consisting of vegetable oil, glycerol triacetate, citric acid derivative, phosphoric acid derivative, ester of vegetable oil, glycol, glycol derivative, paraffin wax, a pentaerythritol ester of a fatty acid, stearic acid derivative, glycerol monostearate, polyethylene glycol, and combinations thereof.

96. The method according to claim 61, wherein the adhesive component comprises at least one hydrophilic adhesive agent selected from the group consisting of natural gum, synthetic polymeric gum, synthetic polymer, mucoadhesive polymer, saccharide derivative, cellulose derivative, and combinations thereof.

* * * * *